US00PP15176P2

(12) United States Plant Patent
van Rijn

(10) Patent No.: US PP15,176 P2
(45) Date of Patent: Sep. 28, 2004

(54) ***ANTHURIUM* PLANT NAMED 'EXCITING LOVE'**

(50) Latin Name: *Anthurium andreanum*
Varietal Denomination: Exciting Love

(75) Inventor: Leonardus W. B. M. van Rijn, Schipluiden (NL)

(73) Assignee: Rijnplant B.V., Schipluiden (NL)

( * ) Notice: Subject to any disclaimer, the term of this patent is extended or adjusted under 35 U.S.C. 154(b) by 0 days.

(21) Appl. No.: 10/721,992

(22) Filed: Nov. 25, 2003

(51) Int. Cl.[7] ..... A01H 5/00
(52) U.S. Cl. ..... Plt./365
(58) Field of Search ..... Plt./365

*Primary Examiner*—Anne Marie Grunberg
(74) *Attorney, Agent, or Firm*—C. A. Whealy

(57) ABSTRACT

A new and distinct cultivar of *Anthurium* plant named 'Exciting Love', characterized by its upright and outwardly spreading plant habit; freely clumping growth habit; durable dark green leaves; grayed purple-colored spathes with green-colored margins and pale yellow-colored spadices that are positioned slightly above and beyond the foliage on strong and erect scapes; freely flowering habit; and good inflorescence longevity.

2 Drawing Sheets

Botanical classification/cultivar designation: *Anthurium andreanum* cultivar Exciting Love.

BACKGROUND OF THE INVENTION

The present invention relates to a new and distinct cultivar of *Anthurium* plant, botanically known as *Anthurium andreanum,* and hereinafter referred to by the name 'Exciting Love'.

The new *Anthurium* is a naturally-occurring whole plant mutation of the *Anthurium andreanum* cultivar Red Love, disclosed in U.S. Plant Pat. No. 11,005. The cultivar Exciting Love was discovered and selected by the Inventor as a flowering plant from within a large population of plants of the cultivar Red Love in a controlled environment in Schipluiden, The Netherlands in September, 1999.

Asexual propagation of the new cultivar by meristem culture in a laboratory in Belgium since September, 1999, has shown that the unique features of this new *Anthurium* plant are stable and reproduced true to type in successive generations of asexual propagation.

BRIEF SUMMARY OF THE INVENTION

The new *Anthurium* has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar Exciting Love. These characteristics in combination distinguish 'Exciting Love' as a new and distinct cultivar:

1. Upright and outwardly spreading plant habit.
2. Freely clumping growth habit.
3. Durable dark green leaves.
4. Grayed purple-colored spathes with green-colored margins and pale yellow-colored spadices that are positioned slightly above and beyond the foliage on strong and erect scapes.

5. Freely flowering habit.
6. Good inflorescence longevity.

Plants of the new *Anthurium* are most similar to plants of the parent, the cultivar Red Love. In side-by-side comparisons conducted in Schipluiden, The Netherlands, plants of the new *Anthurium* differed from plants of the cultivar Red Love in the following characteristics:

1. Plants of the new *Anthurium* had larger spathes than plants of the cultivar Red Love.
2. Plants of the new *Anthurium* and the cultivar Red Love differed in spathe coloration as spathes of plants of the cultivar Red Love were solid red in color.

BRIEF DESCRIPTION OF THE PHOTOGRAPHS

The accompanying colored photographs illustrate the overall appearance of the new *Anthurium,* showing the colors as true as it is reasonably possible to obtain in colored reproductions of this type. Colors in the photographs may differ slightly from the color values cited in the detailed botanical description which accurately describe the colors of the new *Anthurium.*

The photograph on the first sheet comprises a side perspective view of a typical flowering plant of the cultivar Exciting Love.

The photograph on the second sheet comprises a close-up view of typical inflorescences of 'Exciting Love'.

DETAILED BOTANICAL DESCRIPTION

In the following description, color references are made to The Royal Horticultural Society Colour Chart, 2001 Edition, except where general terms of ordinary dictionary significance are used. The aforementioned photographs and the following observations and measurements describe 10-month old plants grown in 14-cm containers in Schipluiden, The Netherlands, in a glass-covered greenhouse with average day temperatures of 23° C., average night temperatures of 21° C. and light levels about 6 kilolux.

Botanical classification: *Anthurium andreanum* cultivar Exciting Love.

Parentage: Naturally-occurring whole plant mutation of the *Anthurium andreanum* cultivar Red Love, disclosed in U.S. Plant Pat. No. 11,005.

Propagation:

*Method.*—By meristem culture.

*Time to initiate roots on a meristem-cultured plant.*—About 28 days at 20 to 24° C.

*Time to develop roots on a meristem-cultured plant.*—About 270 days at 20 to 24° C.

*Root description.*—Thick, fleshy, dark pink to cream-colored; lateral roots, thick and abundant.

Plant description:

*Plant shape.*—Upright and outwardly spreading plant habit, inverted triangle, symmetrical.

*Growth habit.*—Freely clumping, bushy and dense growth habit; about six clumps per plant. Appropriate for 14-cm containers; moderately vigorous.

*Plant height, from soil level to top of leaf plane.*—About 33 cm.

*Plant height, from soil level to top of inflorescences.*—About 41 cm.

*Plant diameter or spread.*—About 38 cm.

*Crop time.*—About ten months are usually required from planting of young plants to finished plants in a 14-cm container.

*Foliage description.*—Arrangement: Alternate; simple. Quantity per plant: About 36. Length: About 13.7 cm. Width: About 8.2 cm. Shape: Deltoid. Apex: Apiculate. Base: Cordate to truncate. Margin: Entire. Texture, upper and lower surfaces: Leathery; glabrous, smooth; durable. Venation pattern: Pinnate. Color: Developing leaves, upper surface: 146A to 146B. Developing leaves, lower surface: Between 147A and 143A. Fully developed leaves, upper surface: Between 147A and 139A. Fully developed leaves, lower surface: 146A. Venation, upper surface: 144A. Venation, lower surface: 144A to 144B. Petiole: Length: About 25.9 cm. Diameter, just below geniculum: About 3.5 mm. Diameter, at plant base: About 4.5 mm. Texture: Smooth, glabrous. Color: 146A to 146B. Geniculum length: About 2.1 cm. Geniculum diameter: About 4 mm. Geniculum color: 146B. Wing length: About 3.6 cm. Wing diameter: About 5 mm. Wing color: 182B.

Inflorescence description:

*Inflorescence arrangement.*—Spathes with spadices held slightly above and beyond the foliage. Flowering structures arise from leaf axils. Freely and continuous flowering during the autumn in Schipluiden, The Netherlands. Typically about nine inflorescences per plant. Inflorescences not fragrant.

*Inflorescence longevity.*—Inflorescences last about two months under winter conditions and about three months under summer conditions; inflorescences persistent.

*Spathe.*—Length: About 6.6 cm. Width: About 7.4 cm. Shape: Obliquely cordate to somewhat reniform. Apex: Abruptly acute to mucronulate. Base: Obliquely cordate. Margin: Entire. Texture, upper and lower surfaces: Leathery; glabrous, smooth. Aspect: Cupped. Color: When opening, front surface: Between 178B and 185A; towards the margins, 144A to 146A; venation, same as lamina. When opening, back surface: 146A to 146B; venation, 46A. Fully developed, front surface: 183A; towards margins and base, between 143A and 146A; venation, same as lamina; becoming closer to, but more purple than, 200B; towards margins and base, 144A to 146A. Fully opened, back surface: 146A; venation, 47A to 47B.

*Spadix.*—Length: About 4.2 cm. Diameter: About 7 mm. Shape: Columnar, tapering towards the apex; apex, obtuse. Cross section: Rounded. Aspect: About 10° from vertical. Color: Immature: 11A; towards the apex, 1B to 1C. Mature: 4C; towards the apex, 11B.

*Flowers.*—Quantity per spadix: Numerous, about 200. Shape: Rounded. Height: Less than 0.5 mm. Diameter: About 0.8 mm.

*Reproductive organs.*—Androecium: Anther color: 11D. Amount of pollen: Scarce. Pollen color: 11C. Gynoecium: Stigma shape: Ovoid. Stigma color: N155D. Ovary color: N155D.

*Scape.*—Length: About 30.1 cm. Diameter: About 4 mm. Strength: Strong. Aspect: Erect to slightly outwardly slanted to about 30° from vertical. Color: 146A; towards the apex, darker than 146A and tinged with 175A.

*Seed and fruit.*—Seed and fruit development has not been observed on plants of the new *Anthurium.*

Disease/pest resistance: Under commercial production conditions, plants of the new *Anthurium* have not been observed to be resistant to pathogens or pests common to *Anthurium.*

Temperature tolerance: Plants of the new *Anthurium* have been observed to tolerate temperatures from about 14 to 36° C.

It is claimed:

1. A new and distinct cultivar of *Anthurium* plant named 'Exciting Love', as illustrated and described.

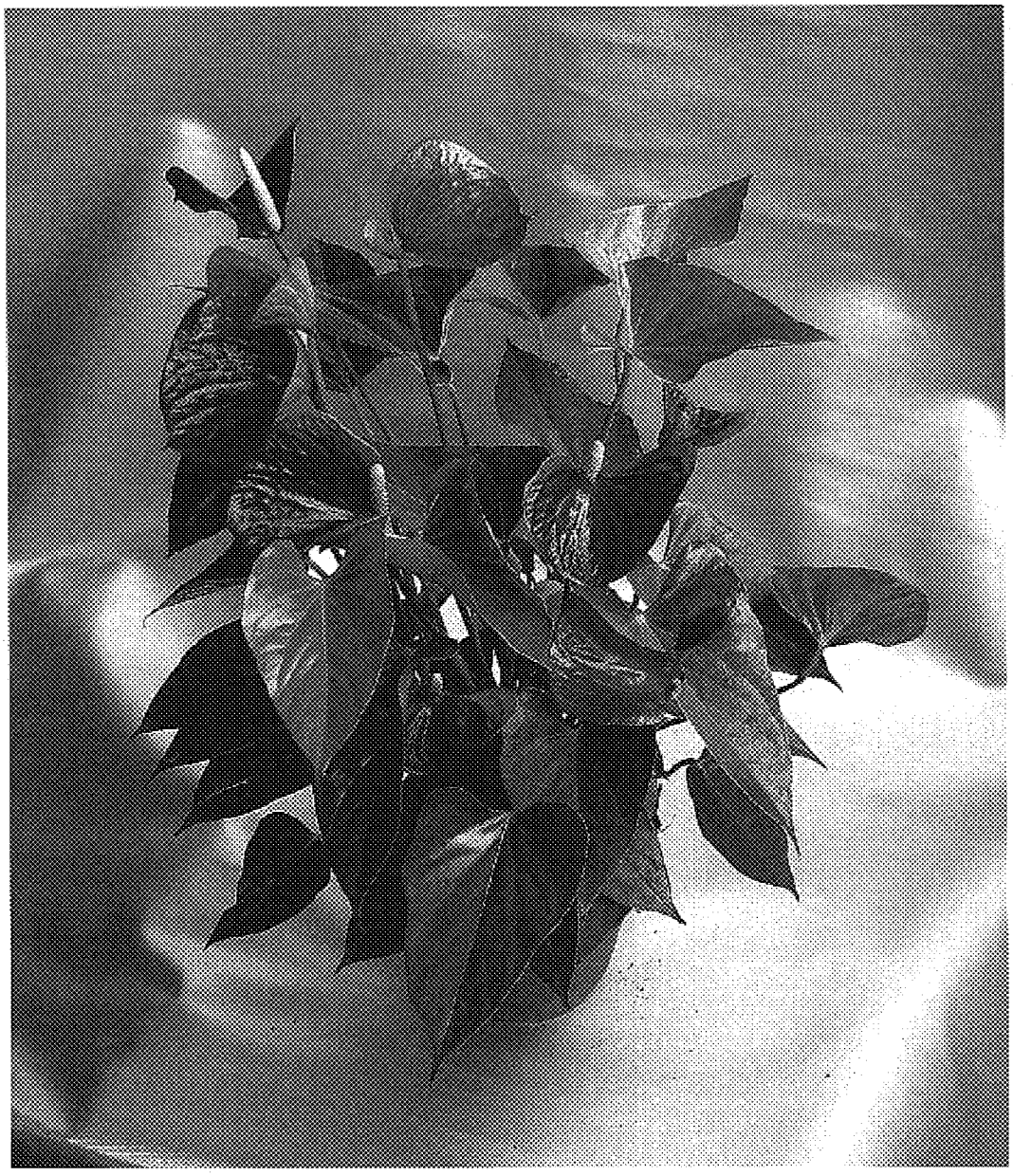

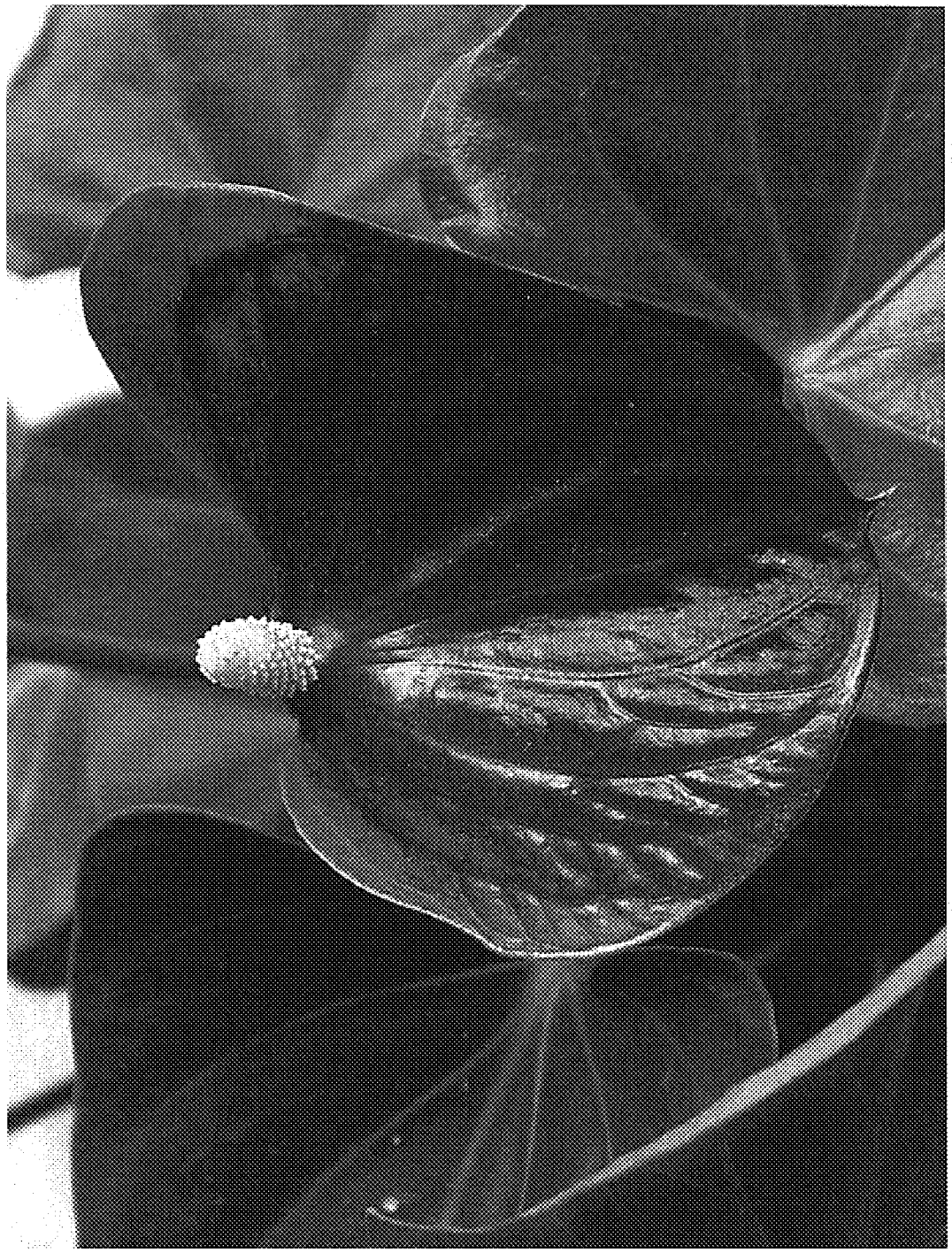

* * * * *